(12) United States Patent
Kroll et al.

(10) Patent No.: US 6,350,168 B1
(45) Date of Patent: Feb. 26, 2002

(54) LIGHT SELECTIVE SPORT GARMENTS

(75) Inventors: Mark W. Kroll, Simi Valley, CA (US); Karl J. Kroll, Maple Grove, MN (US)

(73) Assignee: Kroll Family Trust, Simi Valley, CA (US)

( * ) Notice: Subject to any disclaimer, the term of this patent is extended or adjusted under 35 U.S.C. 154(b) by 0 days.

(21) Appl. No.: 09/680,484

(22) Filed: Oct. 6, 2000

Related U.S. Application Data

(63) Continuation-in-part of application No. 09/472,495, filed on Dec. 27, 1999, now abandoned, which is a continuation-in-part of application No. 08/927,243, filed on Sep. 11, 1997, now Pat. No. 6,007,395.

(51) Int. Cl.[7] .................................................. B63C 9/08
(52) U.S. Cl. ........................ 441/111; 441/106; 441/112; 2/67; 2/69; 2/108; 2/115
(58) Field of Search ................................ 441/102, 106, 441/108, 111, 112, 114–120; 428/135, 229; 2/67

(56) References Cited

U.S. PATENT DOCUMENTS

| | | |
|---|---|---|
| 4,097,947 A | 7/1978 | Kiefer et al. |
| 4,179,547 A | 12/1979 | Allingham et al. |
| 4,200,360 A | 4/1980 | Mutzhas |
| 4,498,882 A | 2/1985 | Evert et al. .................. 441/116 |
| 4,546,493 A | 10/1985 | Bortnick |
| 4,799,908 A | 1/1989 | Lucius et al. ................ 441/115 |
| 4,834,688 A | 5/1989 | Jones |
| 5,007,109 A | 4/1991 | Wheeler |
| 5,035,345 A | 7/1991 | Janko et al. |
| 5,066,082 A | 11/1991 | Longstaff |
| 5,184,968 A | 2/1993 | Michalochick et al. ...... 441/116 |
| 5,311,394 A | 5/1994 | Naab et al. .................... 441/93 |
| 5,338,239 A | 8/1994 | Cleaveland et al. ......... 441/106 |
| 5,370,566 A | 12/1994 | Mitchell et al. ............... 441/89 |
| 5,374,212 A | 12/1994 | Lall et al. ...................... 441/96 |
| 5,382,184 A | 1/1995 | DiForte et al. ............. 441/108 |
| 5,518,798 A | 5/1996 | Riedel |
| 5,605,482 A | 2/1997 | Choy et al. .................. 441/106 |
| 5,618,909 A | 4/1997 | Lofquist et al. |
| 5,660,572 A | 8/1997 | Buck et al. .................. 441/106 |
| 5,911,612 A | 6/1999 | Steger et al. ................ 441/118 |
| 5,960,476 A | 10/1999 | Danzy |
| 5,964,628 A | 10/1999 | Scanlon et al. ............. 441/129 |

FOREIGN PATENT DOCUMENTS

FR 2540335 8/1984

*Primary Examiner*—Jesus D. Sotelo

(57) ABSTRACT

A life vest for water sports is taught which is translucent to ultraviolet radiation and visible light. This allows the wearer to achieve uniform tan without having the harsh tan lines where the edges of a life vest would normally be. This allows an individual to enjoy both safety and tanning without having to make a choice between the two.

27 Claims, 14 Drawing Sheets

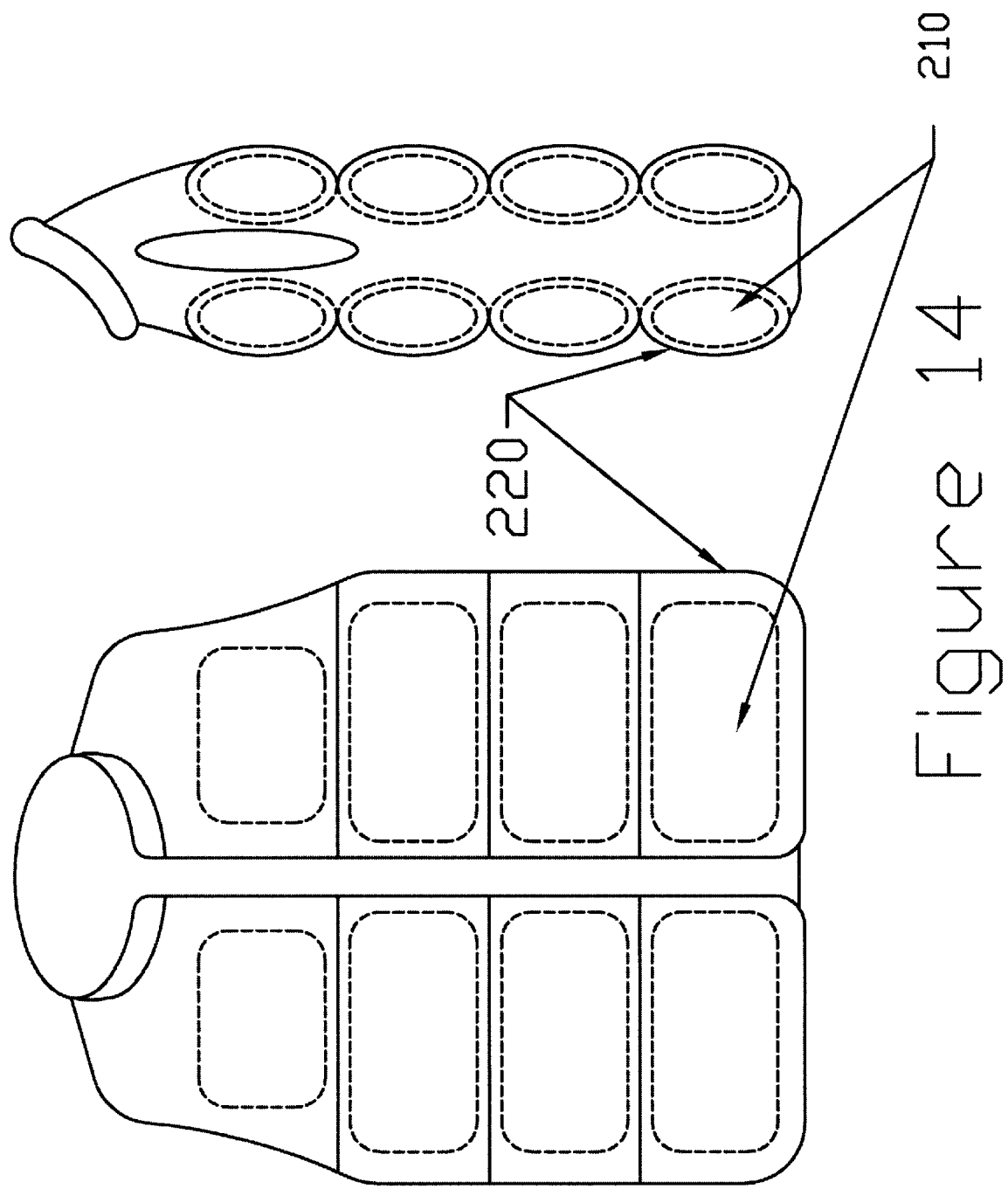

LIGHT SELECTIVE SPORT GARMENTS

This application is a continuation-in-part of the application # 09/472,495 entitled, "Sun Tanning Life Vest" filed Dec. 27, 1999, now abandoned, which is itself a continuation-in-part of the application Ser. No. 08/927,243 entitled, "Sun Tanning Life Vest" filed Sep.11, 1997 now issued as U.S. Pat. No. 6,007,395.

BACKGROUND OF THE INVENTION

People are encouraged to wear life jackets when they are engaged in water sports such a water-skiing, boating, or jet-skiing. However, the same individuals are usually interested in an even suntan. When someone wears a traditional life jacket the area under the life jacket receives no tan and the other areas are very darkly tanned leaving embarrassing lines between the two regions.

Clothing, especially bathing suits, is now available that allows the passage of ultraviolet radiation to facilitate a full body suntan. However, no one has taught a practical lifevest that will transmit ultraviolet rays to give an even tan.

There is another issue—aesthetics. An individual may not wish to cover up their body or swimsuit with a light-blocking life vest. Thus, there is a need for a safe and practical life vest that would allow the passage of visible light.

Snow skiers and mountain climbers could also benefit from light selective articles. Garments that would pass heat-carrying ultra-violet radiation but block the loss of the body's infrared radiation would be very useful. Alternatively, garments that would pass visible light would be attractive for the style conscious resort skier that wished to show off their under-jacket garments.

In spite of the numerous possible uses for light selective sport garments there have been none taught beyond the famous light transmitting swimsuit invention of Reidel (U.S. Pat. No. 5,518,798). Reidel's fabric is actually not light transparent but based on the clever trick of a very loose fabric (hexagonal weave) so that only ⅓ of the skin is covered. Camouflage patterns on the suit then provide privacy by preventing the discernment of small physical features. Bortnick (U.S. Pat. No. 4,546,493) taught another swimsuit approach with a conventional rectangular weave but with coated fibers.

Other mentions of light passage in garments have been directed essentially to novelties. Danzy (U.S. Pat. No. 5,960, 476) teaches a transparent patch in part of a garment to better display tattoos. Jones (U.S. Pat. No. 4,834,688) teaches a transparent pouch sewn onto a T-shirt to hold, for example, a liquid appearing like beer. Wheeler (U.S. Pat. No. 5,007, 109) teaches what is essentially sunglasses attached to a cap.

SUMMARY OF THE INVENTION

The basic object of this invention is the use of light selective materials and fabrics to increase the utility of a garment or sports article. The invention is the novel idea that light selective materials and fabrics can radically improve the usefulness, pleasure, and appeal obtained from sportswear and other garments.

To illustrate the broad applications of this concept the following Table I may be useful by depicting a few examples:

TABLE I

Sample Uses of the Invention

| Light wavelengths → | Infrared | Visible | UV-A | UV-B | Gas Filler |
|---|---|---|---|---|---|
| Tan-Thru ™ life vest | optional | Block | Pass | Block | Yes |
| Fast-Tan ™ life vest | optional | Block | Pass | Pass | Yes |
| See-Thru ™ life vest | optional | Pass | Block | Block | Yes |
| See & Tan-Thru ™ life vest | optional | Pass | Pass | Block | Yes |
| Greenhouse ™ Ski Vest | Block | Block | Pass | optional | optional |
| Show-Me ™ Ski Vest | Block | Pass | optional | optional | No |
| Air-Bag ™ ski pants | optional | Pass | optional | optional | Yes |

For a Tan-Thru life vest one would prefer to transmit UV-A for the skin tanning properties but to limit the UV-B. The visible light is blocked for reasons of modesty and consumer choice. For the infrared radiation, we have two choices which can actually correspond to two different products. For colder and cloudy weather we would want to hold the infrared radiation within the body so we would block it to keep the wearer as warm as possible. This also reduces cancer risk as infrared can be carcinogenic. For sunny but chilly weather, when there is more infrared from the sun, we may wish to transmit this infrared heat to warm the user short-term. All of the life vests are either permanently or temporarily filled with a gas (including air or a foam material) to provide flotation.

For the Fast-Tan™ life vest, the UV-B would also be passed as the UV-B is a strong promoter of melanization.

For the See-Thru™ life vest, the visible light is passed but both of the UV wavelengths are blocked. The infrared treatment is optional as discussed above. For the See & Tan-Thru™ life vest both visible and UV-A light are transmitted but the UV-B is blocked.

The Greenhouse™ snow-ski vest (alternatively a coat with full length sleeves) would transmit UV-A as it provides high energy heating at high altitudes. The warm body then attempts to retransmit infrared (being of lower temperature than the sun and hence giving off lower frequency photons) which is blocked. Visible light is blocked to allow for the more modest consumer. The UV-B passage is optional. Blocking this reduces ultraviolet damage to light sensitive clothing beneath the vest. Gas filling is optional as it presents more insulation but also more bulk. Note that a single layer of UV-A passing material, that blocks IR, can warm the user without any gas filling being required.

The Show-Me™ ski vest or jacket passes visible light to allow the wearer to reveal clothing or physique beneath. The infrared is blocked to retain heat. The UV-A passage is optional depending on the amount of warming desired. No gas filler is indicated for this device.

The Air-Bag™ snow ski pants are gas filled. They offer light weight warmth and cushioning for falls. They protect the hips from falls as air is a very good shock absorber. They would pass visible light to prevent apparent bulk. Other light wavelength passage choices are optional.

It should be clear from the above samples that this invention presents a major new avenue in sport garments. The chart gives seven samples. However, if one were to amplify on this by considering more possible choices, the number of possibilities are impressive. For example, with the five choices of light wavelength transmission and gas filling there are 32=2*2*2*2*2 combinations. There are many choices for the garment or sport article to apply this invention to. Just counting the following: life vest, snow ski vest, snow ski jacket, snow ski pants, hat, gloves, umbrella, and tent gives 10 choices. Multiplying the 10 choices by the 32 combinations gives us 320 illustrations of this invention. The reader will appreciate that it is not necessary to list every one of these applications.

Beyond that flexibility, there are choices and materials that would divide the various light frequencies into different bands. For example, one might pass the lower frequency part of UV-B ( 310–320 nm wavelength) while blocking the more dangerous UV-B which has the 290–310 nm wavelengths. This would allow stimulation of tanning without the higher cancer risk of the full UV-B band.

BRIEF DESCRIPTION OF THE DRAWINGS

FIG. 14 shows the use of gas pockets distinct from the outside fabric.

DETAILED DESCRIPTION OF THE DRAWINGS

Figure 1:
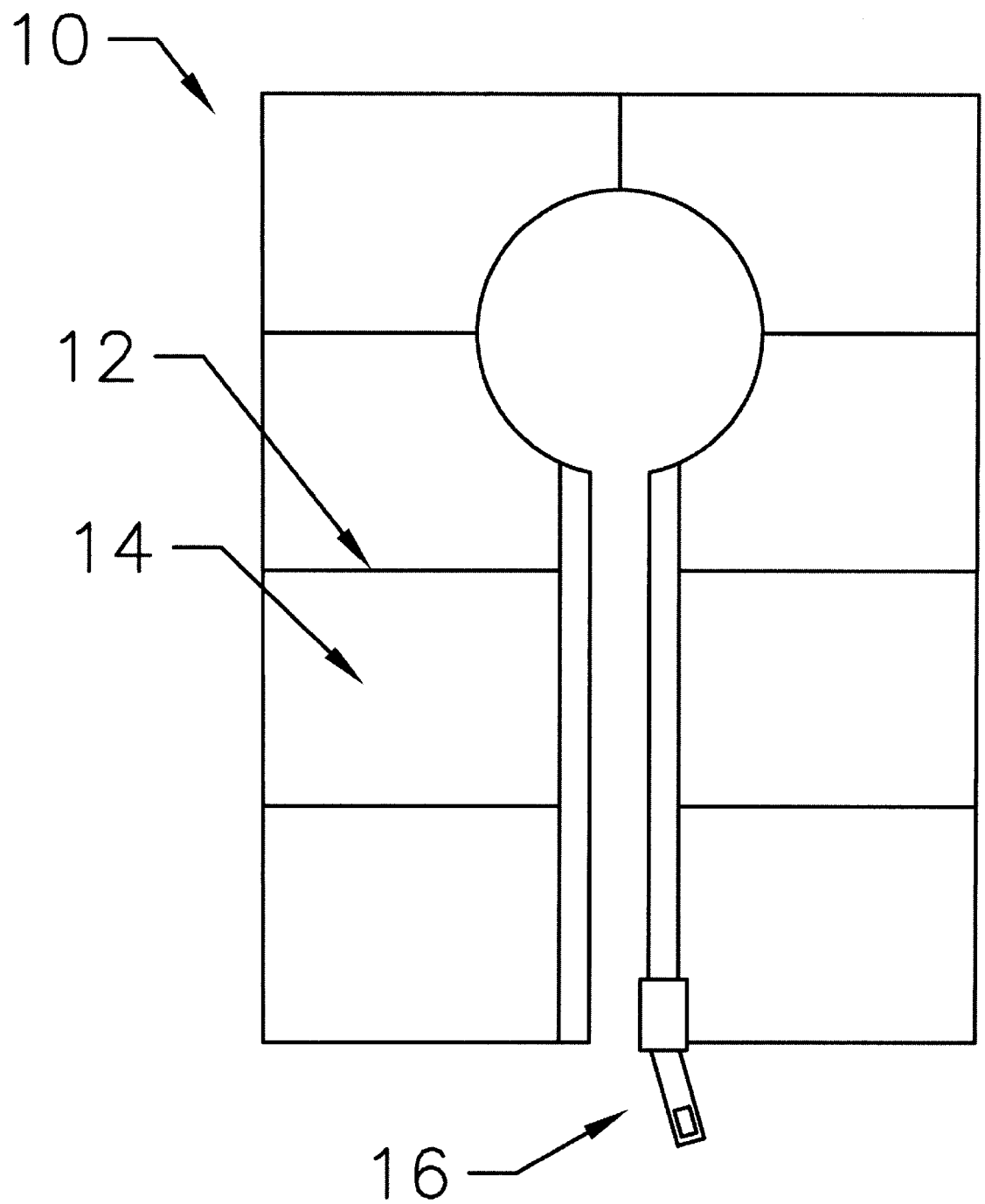
FIG. 1 shows an embodiment of a life vest embodiment of the invention, which is continuously inflated.

FIG. 1 shows one embodiment of the present invention. Here a lifevest 10 is made using a film that is translucent to ultraviolet light. A good example of such a film is polyvinylidene fluoride. PVDF is distinctive among polymers in that rather than degrading from ultraviolet light it actually gets stronger by cross-linking. An oriented PVDF film is a good transmitter of ultraviolet (UV) light and can have a transmittance as high as 85% –90%.

Other useful materials include Ecdel from Eastman Chemical Company of Tennessee, TPX of Mitsui Plastic's Inc. of Japan, Teflon of DuPont Engineering Polymers, and Tenite of Eastman Chemical Company of Tennessee. Another suitable material would be a light stabilized polyamide based material. Such a light stabilized material is available from Allied Signal Incorporated of Morristown, N.J.

The practitioner in the art can find many useful references to assist in the choice of an appropriate material or fabric. For example, a material that will transmit visible and UV light but block infrared is taught in Allingham, et al. Mutzhas and Longstaff each teach appropriate materials for transmitting UV-A (lower frequency ultra-violet) and violet (visible). The following discussion of some of these material choices is liberally taken from them.

Polymers passing solar radiation, yet blocking infra-red radiation, can begin with a matrix of polyethylene or a copolymer in which polyethylene predominates, containing a sufficient quantity of a metaphosphate of a metal chosen from among group 1 to 3 of the periodic table. The addition of certain phosphates, and especially metaphosphates does not perceptibly impair the transmission of solar radiation, but changes in a very pronounced manner the transmission of infra-red radiation.

If the polyethylene or polyethylene copolymers have a finely dispersed phosphate ion (such as $PO_4^{-3}$) it will have a strong absorption in the IR region, while being substantially transparent in the visible range. The phosphates used are typically insoluble forms of sodium- potassium- calcium- or aluminum-metaphosphate. The quantity of these incorporated in the polymeric matrix may be varied between 1 and 20 percent by weight, the preferred range being 3 to 10 percent by weight. The preferred polyethylene is low density polyethylene or copolymers of ethylene with vinyl acetate. The insoluble forms of the above metaphosphates can be blended with a granulate of polyethylene by standard industrial processes, such as milling or double screw extrusion. The material can be blow-extruded and the resulting films have good mechanical strength. Experiments have shown that films of low density polyethylene containing from 5 to 10 percent by weight of sodium metaphosphate, or of potassium metaphosphate have good mechanical properties; they are substantially transparent to solar radiation, yet absorb at least 80 percent of infrared radiation.

Metaphosphates, or polymethaphosphates of aluminum, calcium, barium, etc. may also be suitable.

For the Tan-Thru™ embodiment the plastics material, which preferable is a thermoplastic material or acrylic resin in the form of either a thin film or woven or knitted material, should exhibit the property of being transparent to long wave UV-A radiation of wavelengths between 320 and 400 nm and to visible light in the range between 400 and 450 nm which are those particularly associated with immediate pigment tanning. In addition, the visible light associated within the range 450–700 nm and a major portion of the IR wavelengths greater than 700 nm are absorbed.

Suitable materials are resins of vinyl chloride, polyolefins such as polyethylene and polypropylene, or acrylic resins such as polymethyl-methacrylate. The vinyl chloride resins referred to are homopolymers or copolymers of vinyl chloride and such resins may, in addition, contain plasticizers preferably of phathallate esters. Copolymers such as polyethylene/vinyl acetate and butadiene/styrene would also suffice. A preferred material is a plasticized polyvinyl chloride film of thickness between 100 and 300 microns, for example, 175 microns, and this may be a single film or a laminate formed with a reinforcing nylon or polyester net to give greater physical strength.

Whichever of the resins is used, it should not have a significant absorption, i.e., greater than 30%, of radiation of wavelengths between 310 and 450 nm. The resin should also be light-stable and non-volatile at the relatively high temperatures used in extrusion or callendering (i.e. about 150°–200° C.). Because these resins are transparent to substantially all of the available energy in the UV-A and UV-B wavelengths and most of the visible and IR spectrum, additional agents described below need to be added to the formulations to selectively filter the wave bands of light previously mentioned in order to achieve the desired effects.

As an alternative to rigid or plasticized thermoplastic film, a woven or knitted fabric preferably of nylon or polyester filaments may be used. A suitable support material is the polyester polyethylene terephthalate. Care must be taken to ensure that the particular cross-section of the fiber, the number of fibers per element and the orientation of the fiber in the woven or knitted fabric does not cause excessive light reflection or defraction. One example is ICI polyester.

A second fabric alternative to rigid film would be Tietex.RTM. 18 gauge warp-knitted polyester. This particular fabric has highly organized linear orientated fibers which minimizes light defraction and encourages high general light transmission.

Because these polyesters have a high UV-B absorbing capacity in their own right, i.e. without additional UV absorbing agents, only those agents imparting visible and IR absorption need be added to create an ideal sunscreen.

The agent used typically in the rigid or plasticized film to achieve UV-B leakage in the range of 310–320 nm is ethylhexyl-p-methoxycinnamate at a weight concentration of 0.05%, when the film thickness is between 100–300 microns. For the same film, pigments such as Microlith Violet B-K, Cromoptal Blue A3R (Ciba-Geigy) and PV Carmine HF4C (Hoescht) at a concentration of 0.1% w/w provide ideal visible light absorption as well as imparting attractive coloration, and a heat sink comprising thermal black (finely divided carbon black) at a concentration of for example, 0.5% w/w, to absorb IR radiation. Film compounded from plasticized PVC and containing the above ingredients serves to transmit 20% UV-B in the wavelength range 310-320 nm, but excludes substantially all UV-B in the range 290–310 nm.

Similar levels of UV-B irradiance in the range 310–320 nm would be achieved by deployment of the previously described fiber fabrics, suitably surface printed or dyed with disperse dyes such as Dispersol Red B2-B at 2.25% w/w concentration. Infra-red may be absorbed by carbon black as previously described or reflected by titanium dioxide.

The life vest embodiment is made by having vertical separating walls 12, which break the vest into chambers 14. Each chamber 14 is filled with ultraviolet transmitting gas such as carbon dioxide or air or nitrogen among many others.

A molded plastic zipper 16 is used to secure the vest to the subject. Other methods of securement could be used as well. Straps to go around the back or crotch straps 200 (see FIG. 14) would also be acceptable. They preferably would be made of an oriented PVDF or other UV transmissive materials.

The vest in FIG. 1 shows one embodiment for an over-the-neck type of life jacket. The same idea of the invention could easily be applied to a traditional vest type that goes all around the back without departing from the spirit of the invention. This is shown is later figures.

Figure 2:
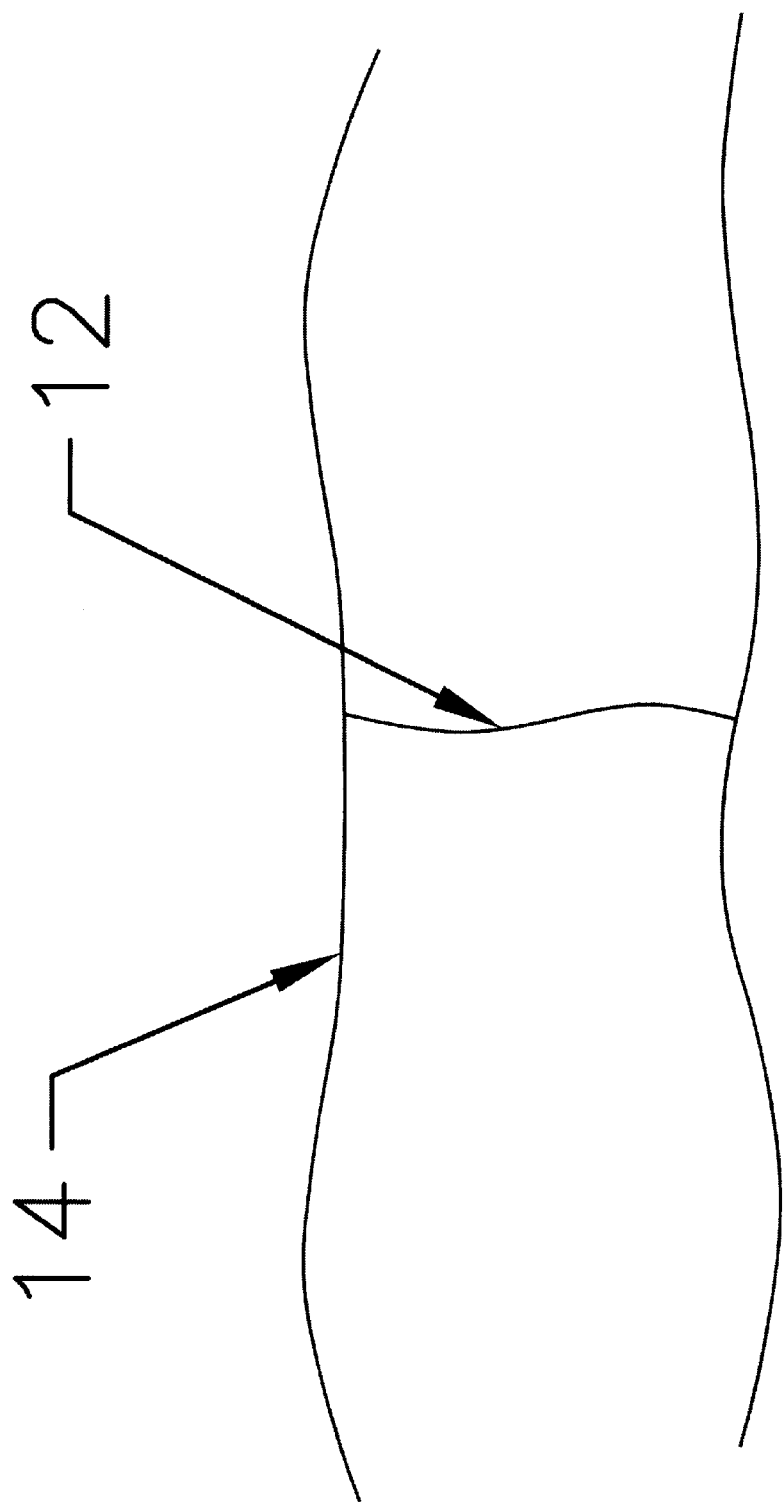
FIG. 2 shows the side view of the continuously inflated life vest embodiment.

FIG. 2 shows a side view of the cells of the invention as shown in FIG. 1. Bulkhead walls 12 again are separating the vest and the chambers 14 from each other which are each filled with the inert gas.

Figure 3:
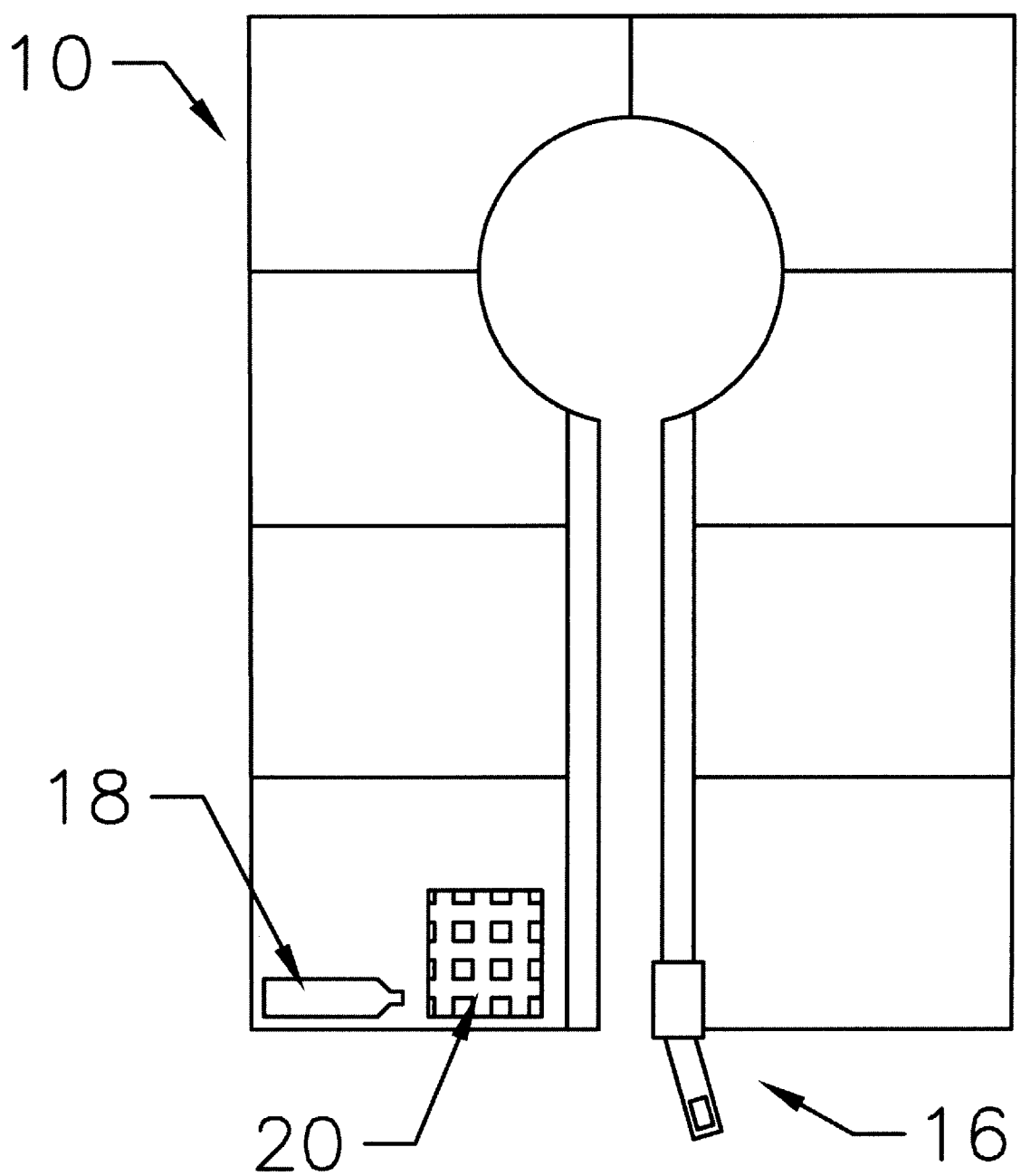
FIG. 3 shows a plan view of the acutely inflating life vest embodiment of the invention.

FIG. 3 shows an embodiment of the present invention that inflates only in response to water immersion. This "acute" embodiment uses a compressed carbon dioxide reservoir 18, which is triggered by the water sensor 20 to release the carbon dioxide into the vest to inflate it. Other compressed gases could be used as well.

This vest would be very comfortable and lightweight for subjects and yet would inflate instantly upon immersion in water. Even if the material is not 100% transmissive to the ultraviolet light, one can match the transmission by using the appropriate degree of sunblock on the exposed limbs. For example, one might use a 4 or 6 level sunblock on the arms to avoid having any contrasting tans.

Figure 4:
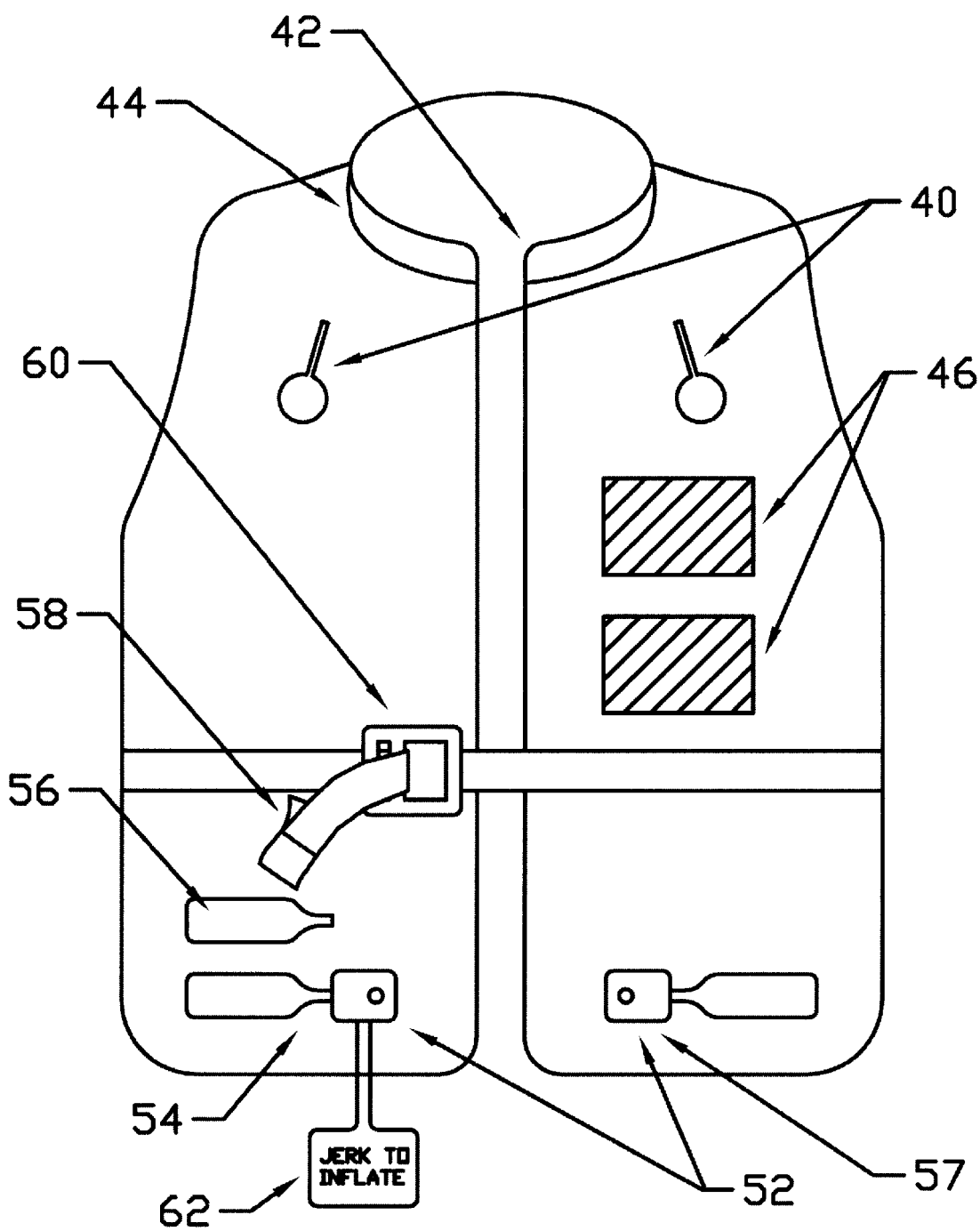
FIG. 4 shows details of the emergency inflating version.

FIG. 4 shows a more detailed version of the inflatable embodiment of the invention. The vest has manual inflation straws 40 as well as emergency inflation handle 62. The emergency inflation handles 62 allows the gas from the CO2 cartridge 54 to immediately fill the vest. A spare CO2 cartridge 56 can also be incorporated in the vest. Item 57 is an automatic inflation means. This system works by either sensing the water electrically or through a fast chemical solution to allow the CO2 to be injected into the vest. The closure 60 needs to be strong enough to hold 1600 newtons of force (360 lb.) alone or through the combined strength of multiple closures.

Passive intrinsic flotation means 46 are an alternative also included in the vest. These can be made of light transmissive foam. The vest includes very reliable securement means to pull the two sides of the vest across the users chest 60 along with a retainer 58 for each adjustable closure 60 to prevent it from being easily removed. All corners 42 are rounded to prevent irritation or cutting of the user and edges 44 are heat sealed to prevent leakage.

Figure 5:
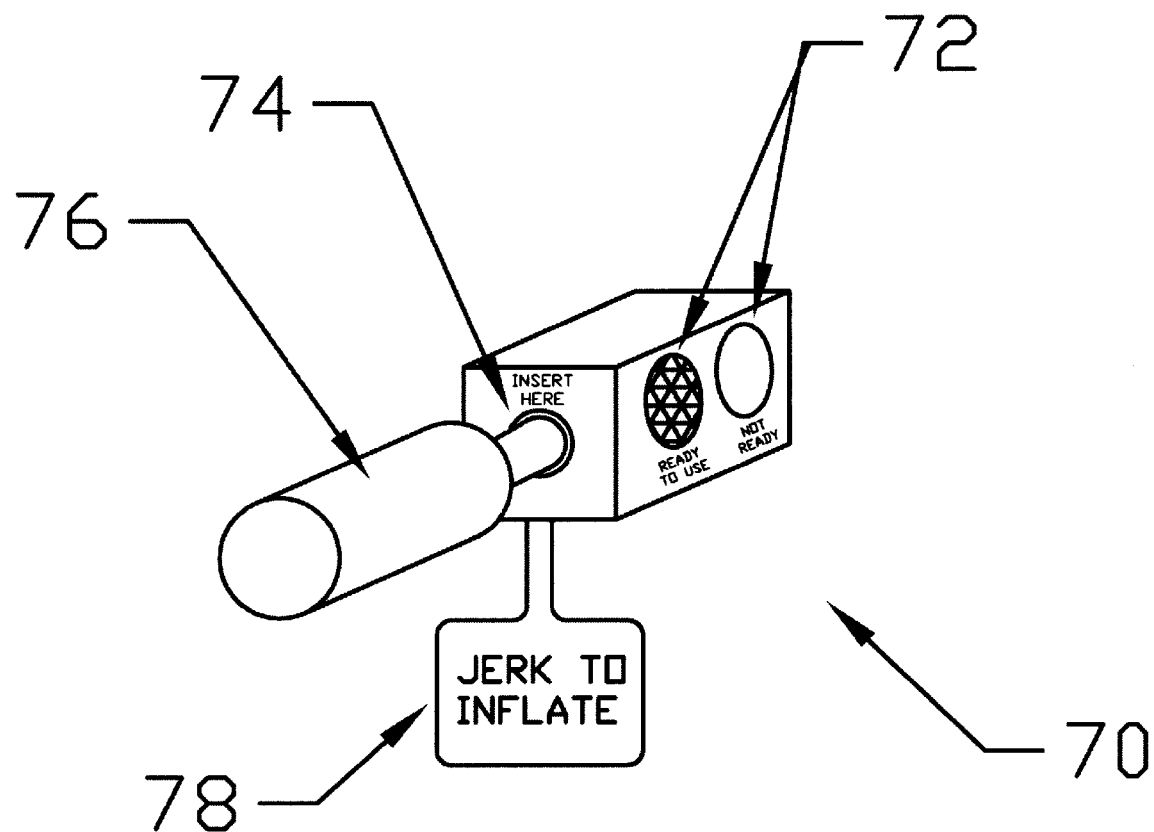
FIG. 5 shows the details of the rapid inflation mechanism.

FIG. 5 shows the details of the rapid $CO_2$ inflator. The system 70 has an indicator 72 to indicate whether the system is ready to use or not. The 12-gram $CO_2$ cartridge 76 is inserted into an insert 74. The handle 78 is jerked to instantly inflate.

Figure 6:
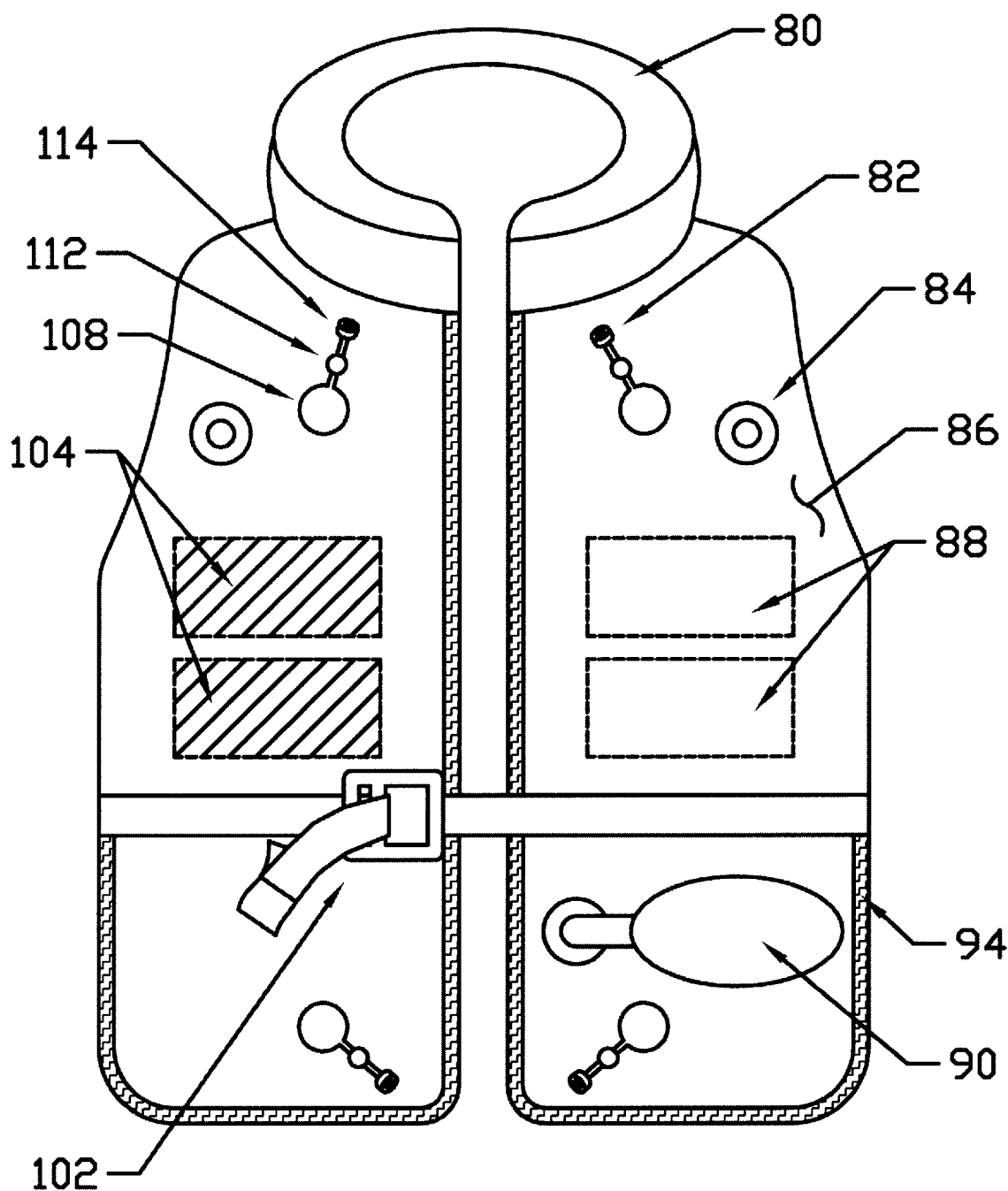
FIG. 6 shows details of the manually inflating hybrid version.

FIG. 6 shows more details of a deluxe embodiment of the invention. It begins with an inflated collar 80 to help right the wearer in the water. The passive inflation mechanism 82 is shown in four locations: the top and bottom of the vest and the left and right sides. Each mechanism 82 has a non-toxic mouthpiece 114 and a deflation squeeze bulb 112. Each is bonded to the vest with a transparent collar 108.

The vest may have passive flotation elements, which are merely a sealed gas such as the pockets 88 or of transmissive foam such as those in pockets 104. An integral pump 90 can be used if someone would rather squeeze with their hands then to blow air into the device.

Pressure release valve 84 found on each side of the vest is to release excessive pressure from a $CO_2$ malfunction, excessive manual inflation followed by high temperature, or someone jumping on the vest. This would allow enough air to leak out to prevent damage to the vest. The seams 94 are sewn to meet the Class 300 lockstitch level to meet federal standard 751.

Figure 7:
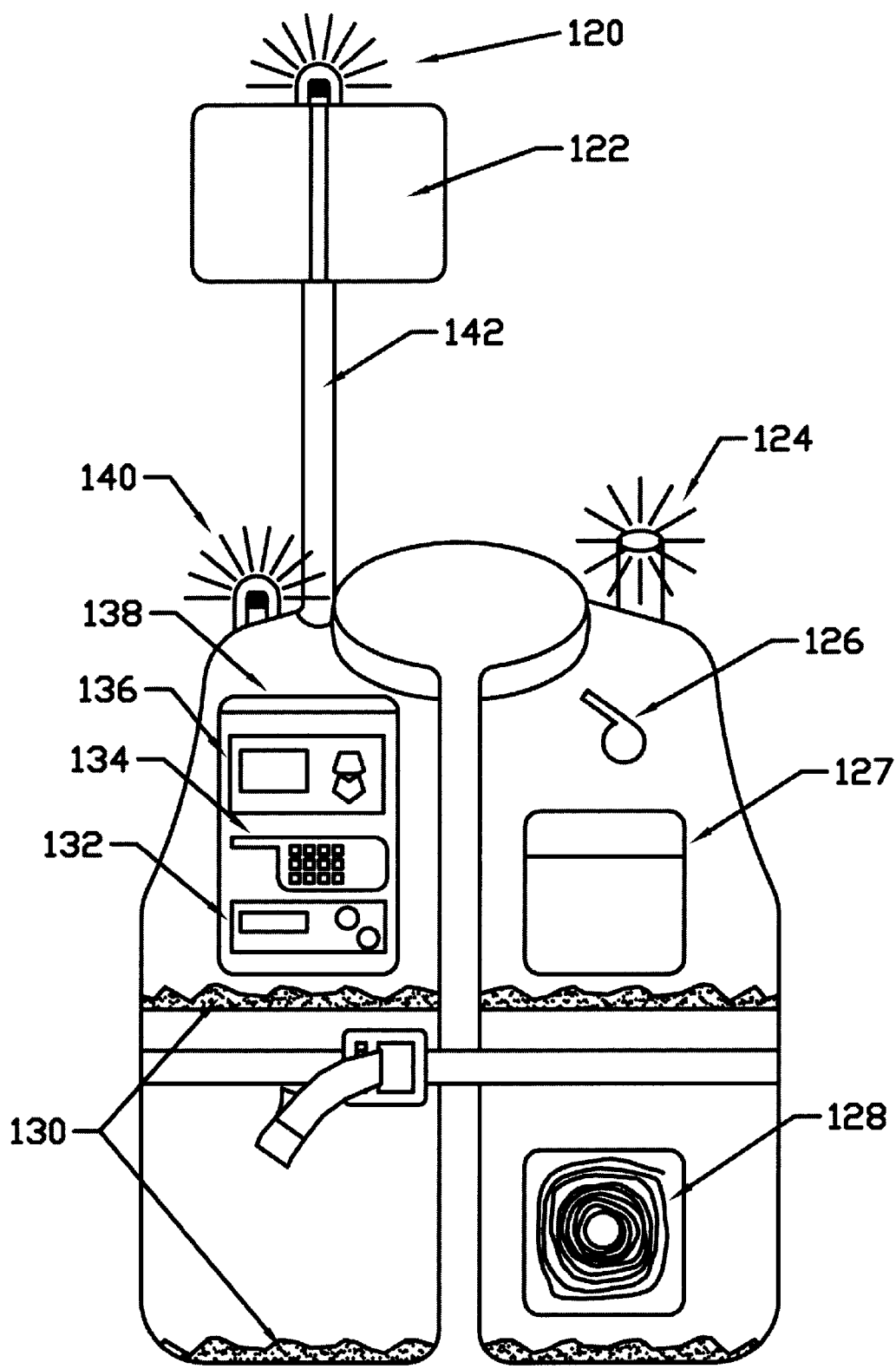
FIG. 7 shows details of a full emergency system with whistle and flashers.

FIG. 7 gives details of the embodiment of the invention optimized to enhance the rescue of the wearer. The automatic inflation causes the mast 142 to inflate which positions flashing light 120 above the head of the wearer. This also positions metalized flat surface 122 above the head of the wearer to better reflect radar. Incorporated in the light 122 could also be an ELT beacon or automatically operated cell phone to generate a distress call. Conventional strobe light 124 or glowing light 140 are shown as alternative embodiments to be attached to the main part of the vest. Whistle 126 is also available for the wearer's use. Pockets 127 can be used by the wearer to store emergency supplies or keys. Pocket 128 holds a long fluorescent colored ribbon to further aid in the rescue of the wearer. A first aid kit 136 could be included as well as cell phone 134 and patch repair kit 132.

The automatic inflation as well as the permanently inflated PFD chambers have integral fluid which is not hard in the presence of $CO_2$ but hardens very quickly in the presence of oxygen or nitrogen. Thus if any leak were detected these would be self-sealing. This would be especially true along the stitch cracks of the stitching 130. This self-healing fluid would not work with breathing inflation as the oxygen and nitrogen from the breath would initiate the sealing process.

Figure 8:
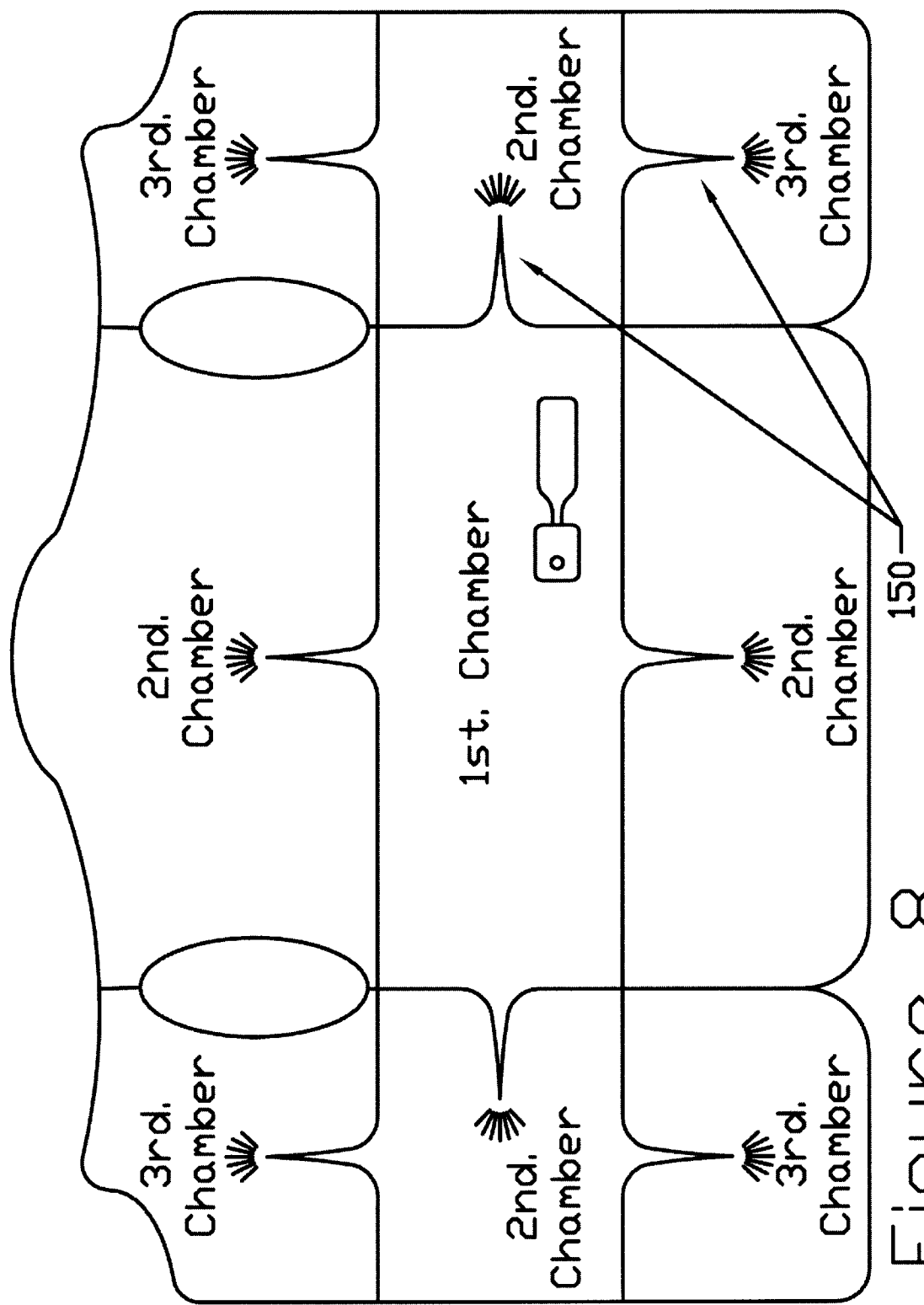
FIG. 8 shows system with multiple chambers with protective valves.

FIG. 8 shows means of allowing a single path of inflation means or pressurized gas means to inflate the vest and yet maintain integrity of the multiple chambers. With this design there is a bi-leaflet reed valve 150 between a pressurized supply chamber and the receiving chamber. This allows the flow of the gas from the pressurized source to all chambers. However, if one of the chambers develops a leak it will not discharge all of the chambers. For example if the primary chamber 1 develops a leak it will only discharge itself.

If, in a worse case situation, one of the third level chambers were to be punctured and completely deflate, it would deflate itself as well as the second level chamber that fed it and the first level chamber. However, this is only 3 of the 9 chambers lost due to the severe deflation on the one chamber and is much preferable to having the whole system deflated.

In the alternative a valve system could go by hose from the pressure and gas source to each one of the individual chambers. This would ensure that the deflation of no chamber could interfere with its neighbors. However, this adds expense and weight and makes transmissibility of visible and ultraviolet light more problematical.

Figure 9:
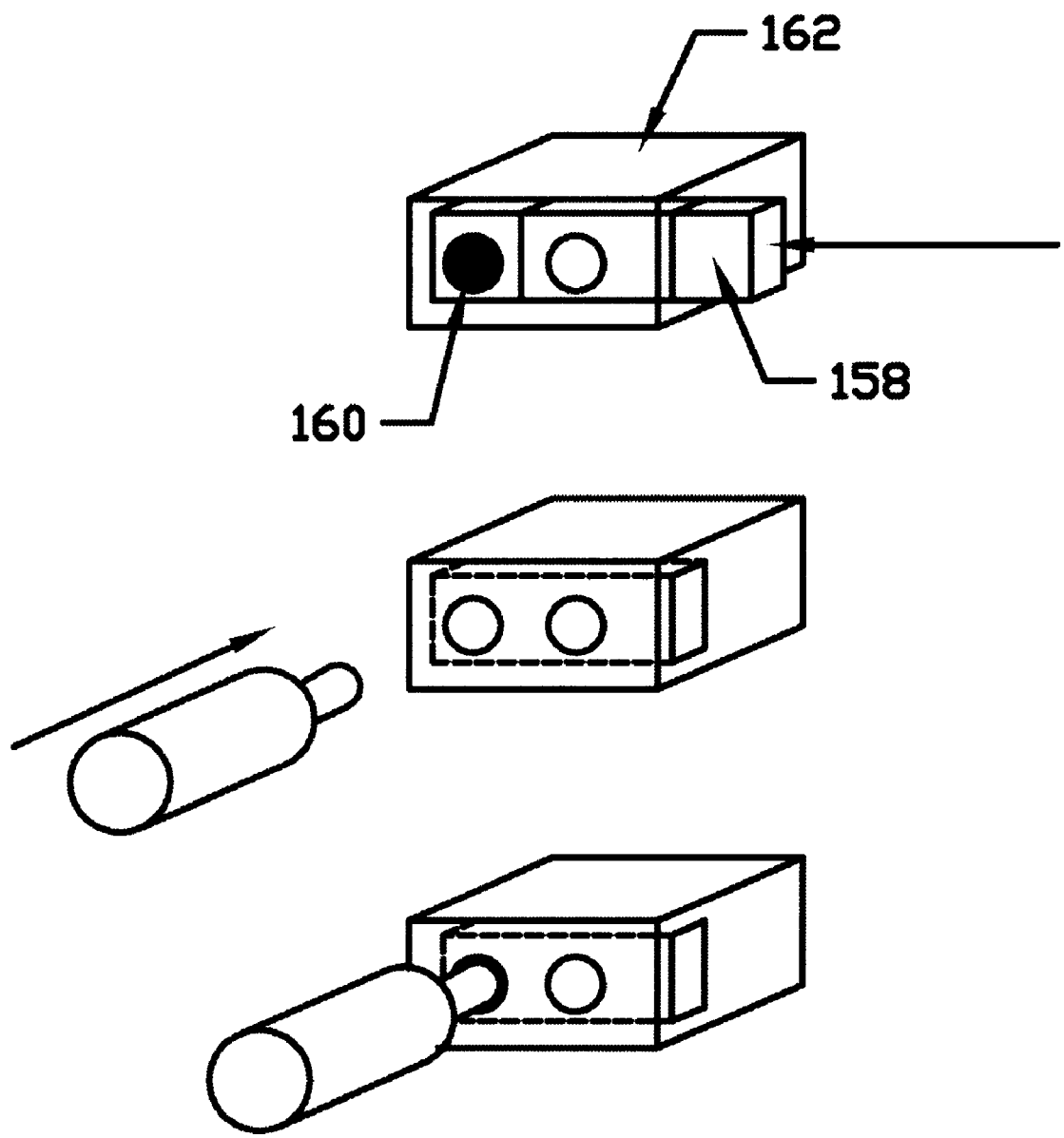
FIG. 9 shows the foolproof mechanism for gas cylinder installation.

FIG. 9 shows the detail of the fail-safe mechanism for the water sensitive element. If the water sensitive element 158 is not fully inserted into the sensor mechanism 162 then the hole 160 will not be able to allow the insertion of the $CO_2$ cartridge.

Figure 10:
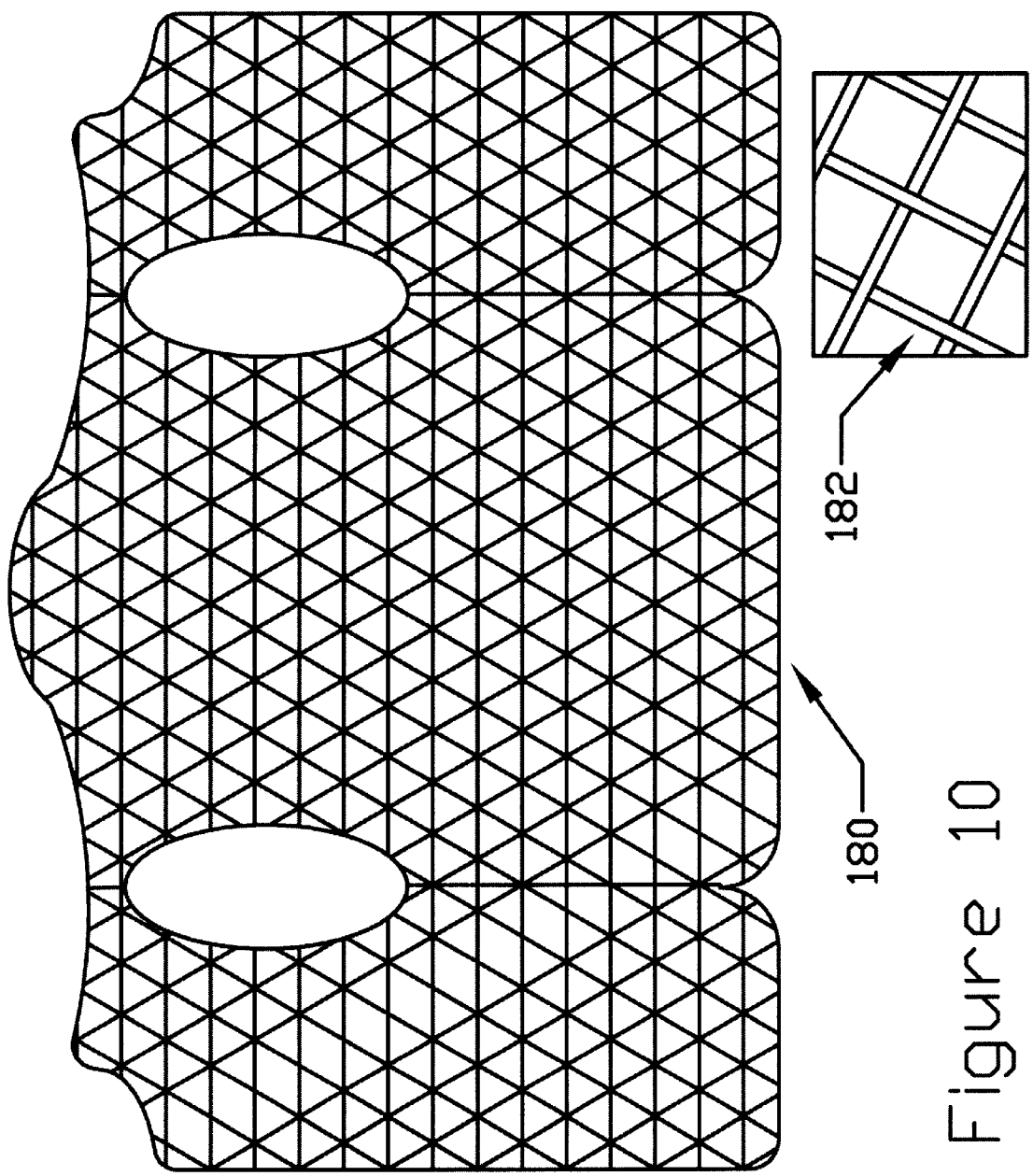
FIG. 10 shows the embodiment of an integral coarse weave fabric to minimize the stickiness of the inside of the clothing embodiments.

FIG. 10 shows the detail of a rough mesh backing to improve wearer comfort. The back of the vest 180 is covered with a very coarse mesh 182 to allow for some air circulation and to decrease the uncomfortable stickiness of the vest.

Figure 11:
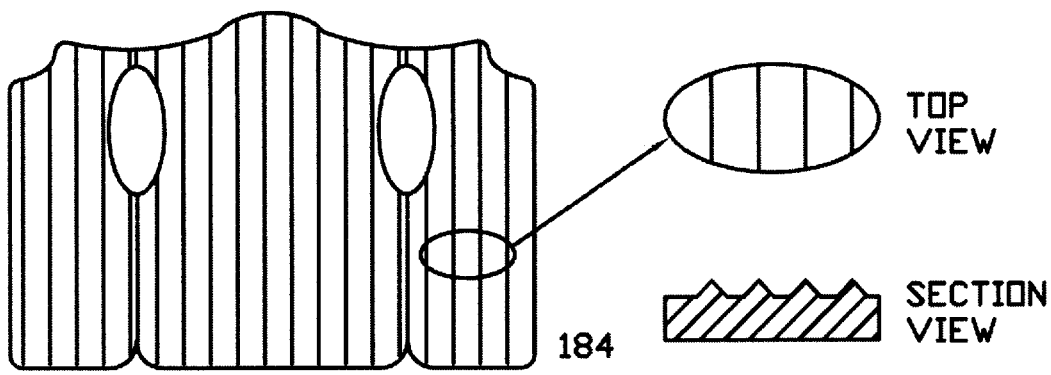
FIG. 11 shows textural solutions to the stickiness problem.
Figure 11:
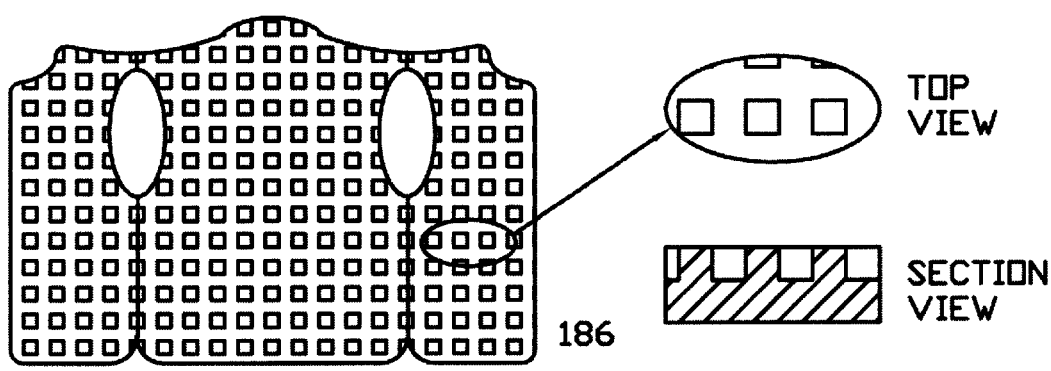
Figure 11:
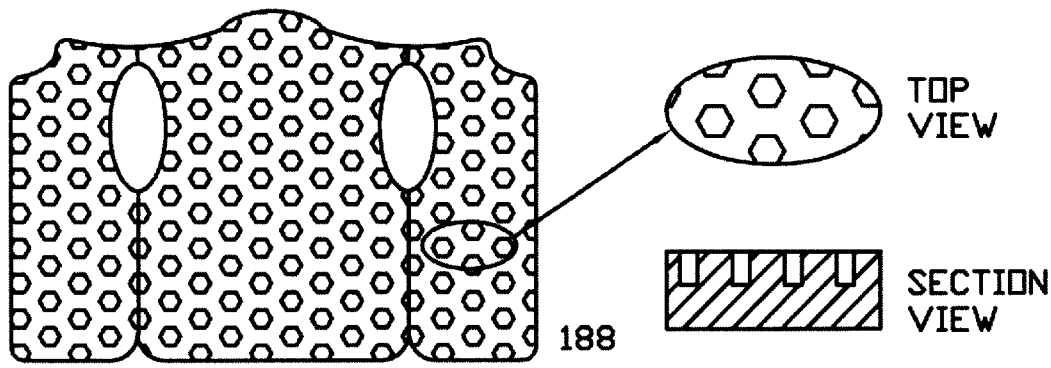

FIG. 11 shows alternative backings to reduce the discomfort from the plastic adhering to the skin. Rib design 184 has a structure to keep the backside of the vest off of the skin. This allows some circulation of the air from top to bottom through the vest. Crosshatched design 186 reduces the area of the vest that is in direct contact with the skin but does not allow any airflow. Dimpled design 188 is the preferred approach as it allows airflow in both directions under the vest.

Figure 12:
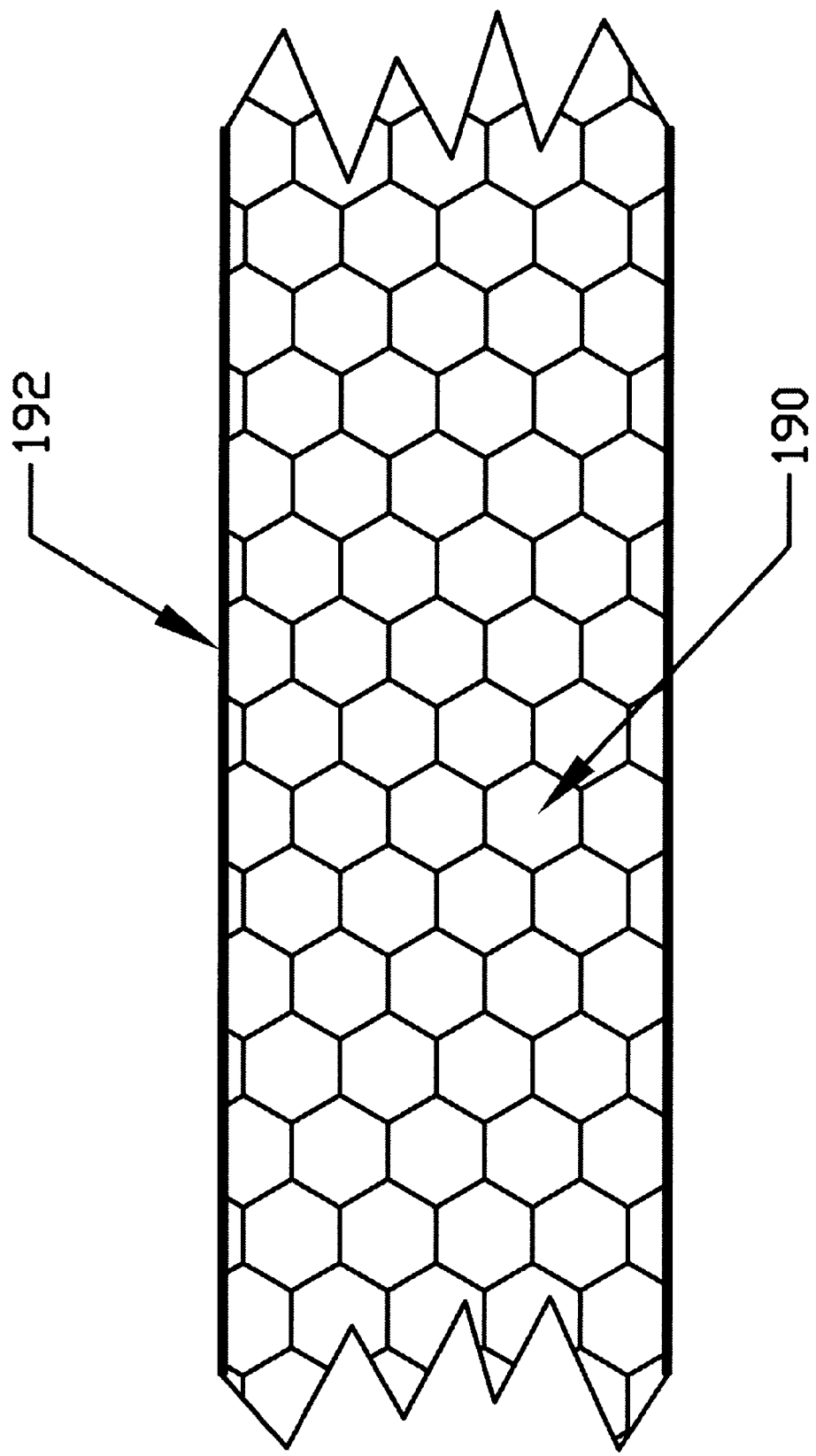
FIG. 12 shows the foam used in one embodiment of the invention.

FIG. 12 shows the closed valve cell foam embodiment of the invention. In this embodiment the chambers are made of closed cell foam 190 which is protected by transparent film 192.

Transparent foam is very difficult to make because of the Snell's law causing multiple pathways for the light as it goes in and out of each cell. However, the foam can be made translucent to allow the passage of ultraviolet light. A representative translucent foam material is high clarity polypropylene combined with endothermic buoying agents which is available from Coral Foam Company located at www.Coralfoam.com.

Also the NuSil Technology Company of Carpenteria, California has a product R1–2354 which is a high strength RTV silicon foam which when catalyzed yields a medium density flame retardant silicone foam which is flexible and translucent.

These foams, while they are not transparent enough to, say, read a newspaper through, will allow, with some distortion, the basic images of a bathing suit to come through and thus achieve some of the vanity and appearance goals of the invention.

Figure 13:
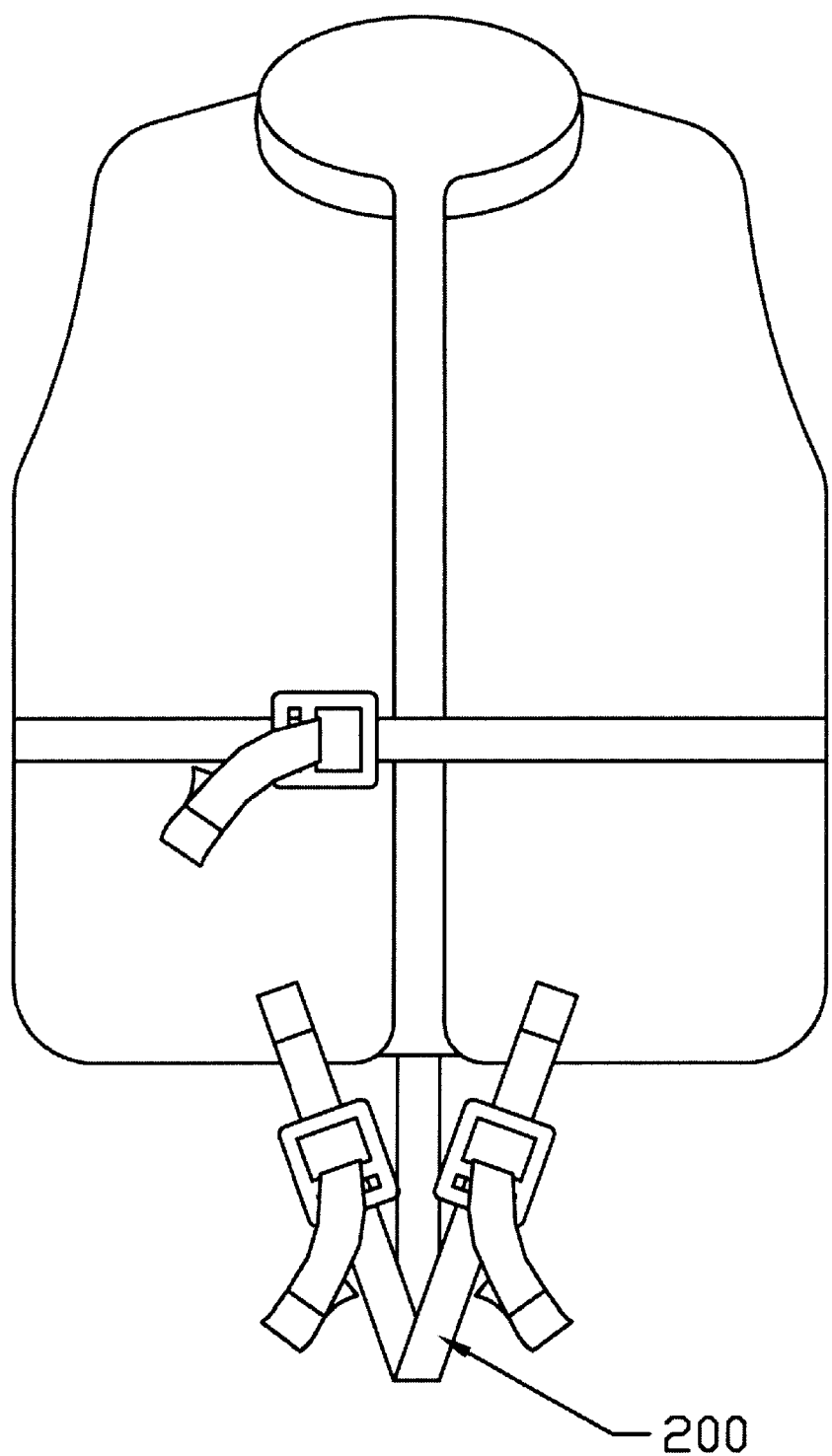
FIG. 13 shows the use of crotch straps for further securing the life vest to the body.

FIG. 13 shows the life vest embodiment of the invention with crotch straps. The importance of these straps lies in the Coast Guard classification of life vests for slow speed usage. In order to have a vest approved for higher speed usage, it must be very securely attached to the body. The crotch strap would allow the life vest of the instant invention to be used with, say, jet skis.

FIG. 14 shows an embodiment of the invention with the gas holding pockets being distinct from the outer fabric. This is because an optimal material for gas impermeability may not be optimal for abrasion resistance. Thus one could select a transparent polyvinyl (moderate abrasion resistance) for the internal gas pouches but use a high abrasion resistant material for the outer layers.

For a Tan-Thru™ life vest one would like to transmit UV-A for the melanization (skin tanning) properties but to limit the carcinogenic UV-B. The visible light is blocked for reasons of modesty and consumer choice. For the UV-A infrared radiation, we have two choices which can really correspond to two products, hence labeled optional.

For the Fast-Tan™ life vest, the UV-B would also be passed as the UV-B is a strong promoter of melanization.

For the See-Thru™ life vest, the visible light is passed but both of the UV wavelengths are blocked. The infrared treatment is optional as discussed above. For the See & Tan-Thru™ life vest both visible and UV-A light are transmitted but the UV-B is blocked.

The Greenhouse™ snow-ski vest (alternatively a coat with full length sleeves) would transmit UV-A. Visible light is blocked to allow for the more modest consumer. The UV-B passage is optional. Blocking this reduces ultraviolet damage to light sensitive clothing beneath the vest. Gas filling is optional as it presents more insulation but also more bulk. Note that a single layer of UV-A passing material can warm the user.

The Show-Me™ ski vest or jacket passes visible light to allow the wearer to reveal clothing or physique beneath. The UV-A passage is optional depending on the amount of warming desired. No gas filler is used for this embodiment.

The Air-Bag™ snow ski pants are gas filled. They offer light weight warmth and cushioning for falls. They protect the hips from falls as air is a very good shock absorber. They would pass visible light to prevent apparent bulk. Other light wavelength passage choices are optional.

Another embodiment of the invention is a tent that passes UV and visible light but blocks ultra-violet. This would warm up during the day yet retain the heat of the inhabitants at night.

It should be understood that the foregoing relates only to preferred embodiments of the present invention, and that many changes and modifications can be made therein without departing from the spirit and scope of the invention as defined in the following claims.

We claim:

1. A buoyant body conforming apparatus comprising: a vest member having at least one enclosed chamber defined by an outer surface, said outer surface being made of a film material which is at least partially transmissive to visible light said at least one enclosed chamber being adapted such that it may be filled with a gas which is at least partially transmissive to light; and means for releasably securing said vest member to the torso of a wearer of said buoyant body conforming apparatus when said vest member is filled with a gas which is at least partially transmissive to visible light whereby said gas filled member at least partially transmits visible light therethrough while simultaneously providing positive buoyancy to the wearer of said buoyant body conforming apparatus for water safety.

2. The buoyant body conforming apparatus of claim 1 in which the gas with which said vest member is filled with is air.

3. The buoyant body apparatus of claim 1 in which the gas with which said vest member is filled with comprises carbon dioxide.

4. The buoyant body conforming apparatus of claim 1 in which the gas which said vest member is filled with comprises nitrogen.

5. The buoyant body conforming apparatus of claim 1 in which the inner skin contacting surface has means to promote air circulation between the surface and wearer's skin.

6. The buoyant body conforming apparatus of claim 1 with means for minimizing direct contact between the apparatus and the wearer's skins.

7. The buoyant body conforming apparatus of claim 1 with means to automatically inflate after a water submersion.

8. The buoyant body conforming apparatus of claim 1 with an emergency commanded inflation ability.

9. The buoyant body conforming apparatus of claim 1 with an active energy using location assistance means.

10. The buoyant body conforming apparatus of claim 1 including a radar reflection means.

11. The buoyant body conforming apparatus of claim 1 in which the means for releasably securing said vest member to the torso of a wearer is capable of withstanding a force of greater than 1,600 newtons.

12. The buoyant body conforming apparatus of claim 1 with a self sealing liquid in at least one of the chamber to automatically repair leaks.

13. The buoyant body conforming apparatus of claim 1 with at least one, one-way valve to at least one of the chambers.

14. The buoyant body conforming apparatus of claim 1 with at least one pressure release valve.

15. The buoyant body conforming apparatus of claim 1 with at least one manual inflation pump.

16. The buoyant body conforming apparatus of claim 1 in which said at least one enclosed chamber of said gas filled vest member is made of a polymer film material which is at least partially transmissive to some wavelengths of light and which will not be significantly degraded by ultraviolet light.

17. The buoyant body conforming apparatus of claim 16 in which said polymer film material is based on a light stabilized polyamide substrate.

18. A buoyant body conforming apparatus comprising: a wearable vest member comprising at least one enclosed chamber each of which enclosed chambers is defined by an outer surface, said wearable vest member being predominately made of a fill material which is at least partially transmissive to light, said at least one enclosed chamber being adapted to be filled with a foam that is at least partially transmissive to light; and means for releasably securing said vest member to the torso of a wearer of said buoyant body conforming apparatus once said at least one enclosed chamber of said vest member is filled with a foam that is at least partially transmissive to light, whereby said foam filled vest member at least partially transmits light therethrough while simultaneously providing positive buoyancy to the wearer of said buoyant body conforming apparatus for water safety.

19. The buoyant body conforming apparatus for claim 18 in which the foam and fill material at least transmit some ultraviolet light in order to allow suntanning the torso the wearer of said buoyant body conforming apparatus.

20. The buoyant body conforming apparatus of claim 18 in which the fill material and foam material are at least partially transmissive of visible light.

21. The buoyant body conforming apparatus of claim 18 in which the foam contains a high clarity polypropylene.

22. The buoyant body conforming apparatus of claim 18 in which the foam contains a RTV silicone.

23. An insulating body conforming apparatus comprising: a vest member having at least one enclosed chamber defined by an outer surface, said outer surface being made of a film material which is at least partially transmissive to visible light said at least one enclosed chamber being adapted such that it may be filled with a gas which is at least partially transmissive to light; and means for releasably securing said vest member to the torso of a wearer of said insulating body conforming apparatus when said vest member is filled with a gas which is at least partially transmissive to visible light whereby said gas filled member at least partially transmits visible light therethrough while simultaneously providing thermal insulation to the wearer of said insulating body conforming apparatus for cold weather comfort.

24. The insulating body conforming apparatus of claim 23 with sleeves to provide coverage for the arms of the wearer.

25. The insulating body conforming apparatus of claim 23 in which the surfaces are chosen to substantially block UV-B light.

26. An insulating body conforming apparatus comprising: two leg members each having at least one enclosed chamber defined by an outer surface, said outer surface being made of a film material which is at least partially transmissive to visible light said at least one enclosed chamber being adapted such that it may be filled with a gas which is at least partially transmissive to light; and means for releasably securing said each leg member to the leg of a wearer of said insulating body conforming apparatus when said leg member is filled with a gas which is at least partially transmissive to visible light whereby said gas filled member at least partially transmits visible light therethrough while simultaneously providing thermal insulation to the wearer of said insulating body conforming apparatus for cold weather comfort.

27. The insulating body conforming apparatus of claim 26 in which the surfaces are chosen to substantially block UV-B light.

* * * * *